United States Patent
Lorant et al.

(10) Patent No.: US 9,364,690 B2
(45) Date of Patent: Jun. 14, 2016

(54) COMPOSITION COMPRISING A SUPERABSORBENT POLYMER AND A GEMINI SURFACTANT

(75) Inventors: Raluca Lorant, Thiais (FR); Laure Fageon, Paris (FR); Karl Boutelet, Paris (FR)

(73) Assignee: L'OREAL, Paris (FR)

( * ) Notice: Subject to any disclaimer, the term of this patent is extended or adjusted under 35 U.S.C. 154(b) by 314 days.

(21) Appl. No.: 13/580,264

(22) PCT Filed: Feb. 22, 2011

(86) PCT No.: PCT/EP2011/052589
§ 371 (c)(1),
(2), (4) Date: Oct. 26, 2012

(87) PCT Pub. No.: WO2011/104228
PCT Pub. Date: Sep. 1, 2011

(65) Prior Publication Data
US 2013/0039963 A1    Feb. 14, 2013

Related U.S. Application Data

(60) Provisional application No. 61/316,005, filed on Mar. 22, 2010.

(30) Foreign Application Priority Data

Feb. 24, 2010   (FR) ...................................... 10 51320

(51) Int. Cl.
| | |
|---|---|
| A61K 9/66 | (2006.01) |
| A61Q 19/00 | (2006.01) |
| A61K 8/02 | (2006.01) |
| A61K 8/06 | (2006.01) |
| A61K 8/44 | (2006.01) |
| A61K 8/68 | (2006.01) |
| A61K 8/81 | (2006.01) |
| A61Q 17/04 | (2006.01) |

(52) U.S. Cl.
CPC ................ *A61Q 19/00* (2013.01); *A61K 8/025* (2013.01); *A61K 8/06* (2013.01); *A61K 8/062* (2013.01); *A61K 8/44* (2013.01); *A61K 8/68* (2013.01); *A61K 8/8147* (2013.01); *A61K 2800/412* (2013.01); *A61K 2800/546* (2013.01); *A61K 2800/654* (2013.01); *A61Q 17/04* (2013.01)

(58) Field of Classification Search
CPC ......... A61K 8/025; A61K 8/06; A61K 8/062; A61K 8/44; A61K 8/68; A61K 8/8147; A61K 2800/654; A61K 2800/412; A61K 2800/546; A61Q 16/00; A61Q 17/04
See application file for complete search history.

(56) References Cited

U.S. PATENT DOCUMENTS

| | | | |
|---|---|---|---|
| 8,512,683 B2* | 8/2013 | SaNogueira et al. | 424/59 |
| 2002/0061321 A1* | 5/2002 | Bara | 424/401 |
| 2009/0068255 A1* | 3/2009 | Yu et al. | 424/450 |

FOREIGN PATENT DOCUMENTS

| | | |
|---|---|---|
| EP | 1908450 A1 | 4/2008 |
| FR | 2891456 A1 | 4/2007 |

* cited by examiner

*Primary Examiner* — Lezah Roberts
*Assistant Examiner* — Nannette Holloman
(74) *Attorney, Agent, or Firm* — Polsinelli PC

(57) ABSTRACT

A cosmetic composition in the form of an emulsion comprising at least one aqueous phase and at least one fatty phase, at least one superabsorbent polymer and at least one surfactant of formula (I):

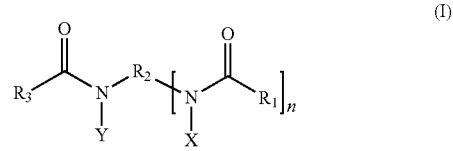

Wherein: $R_1$ and $R_3$ denote, independently of each other, an alkyl radical containing from 1 to 25 carbon atoms; $R_2$ denotes a spacer formed from a linear or branched alkylene chain containing from 1 to 12 carbon atoms; X and Y denote, independently of each other, a group $-(C_2H_4O)_a-(C_3H_6O)_b Z$, in which Z denotes a hydrogen atom or a radical $-CH_2-COOM$, $-SO_3M$, $-P(O)(OM)_2$, $-C_2H_4-SO_3M$, $-C_3H_6-SO_3M$ or $-CH_2(CHOH)_4CH_2OH$, in which M, M' represent H or an alkali metal, alkaline-earth metal, ammonium or alkanolammonium ion, a ranges from 0 to 15, b ranges from 0 to 10, and the sum of a+b ranges from 1 to 25; and n ranges from 1 to 10 is provided.

24 Claims, No Drawings

COMPOSITION COMPRISING A SUPERABSORBENT POLYMER AND A GEMINI SURFACTANT

CROSS REFERENCE TO RELATED APPLICATIONS

This application is a National Phase filing under 35 U.S.C. §371 of PCT/FR2011/052589 filed on Feb. 22, 2011; which in turn claims priority to Application No. 1051320 filed in France on Feb. 24, 2010 under 35 U.S.C. §119; and which in turn also claims the benefit of U.S. Provisional Application No. 61/316,005 filed on Mar. 22, 2010; the entire contents of all are hereby incorporated by reference.

The present patent application relates to a composition in emulsion form comprising a superabsorbent polymer and to the use of the said composition in cosmetics and dermatology, in particular for caring for and treating keratin materials.

It is known practice to use gemini surfactants in cosmetic compositions. In the context of the present invention, the term "gemini surfactants" means compounds comprising two hydrophilic heads and two hydrohobic tails attached together via a spacer. These surfactants have already been described as being useful in cosmetic compositions (WO-A-6/14926, in particular in hair or skin cleansing compositions (EP-0 915 945), or in nacreous concentrates used in cleansing compositions, optionally in combination with hydroxy acids and vitamins such as retinol or tocopherol or derivatives thereof such as diascorbyl palmitate (WO-A-01/74979).

Gemini surfactants have a very specific structure since they comprise two hydrophilic groups and two hydrophobic groups, which gives them not only surfactant properties but also, for some of them, highly appreciated properties associated with their particular structure similar to that of ceramides, which enables them to have properties similar thereto, in particular moisturizing properties, without the formulation drawbacks of ceramides, which are difficult to incorporate and may form crystals. Moreover, these gemini surfactants have a very low surface tension, and they have good emulsifying properties for the preparation of oil-in-water (O/W) emulsions. In addition, they are flexible molecules of very small size, close to that of micelles, and are much less irritant than other surfactants. Furthermore, they show very good affinity for the hair and the skin, reduce lipoperoxidation, i.e. the oxidation of lipids that protect the hair, this oxidation causing dehydration and loss of colour. In addition, they are excellent wetting agents.

However, when they are used in O/W emulsions, these surfactants have the drawback of giving compositions that do not have good cosmetic properties. Specifically, the compositions obtained are heavy on application since they do not slide well over the skin, they spread poorly and are judged to be absorbed too quickly. Consequently, these emulsions are not sufficiently fresh, and, once absorbed on the skin, a coarse, dragging effect is observed. As a result, the consumer has a negative sensation during application to the skin.

There is thus still a need for an O/W emulsion containing a gemini surfactant, which has good cosmetic properties, especially on application. The desired cosmetic properties are a soft and pleasant effect on application, a fresh effect, no coarse or dragging effect, and good glidance during application to the skin.

The object of the present invention is to be able to make emulsions that have good cosmetic properties without having the drawbacks of the prior art.

The Applicant has discovered, surprisingly, that this problem can be solved by combining the gemini surfactant with a superabsorbent polymer.

Thus, one subject of the present invention is a composition in emulsion form comprising at least one aqueous phase and at least one fatty phase, at least one superabsorbent polymer and at least one surfactant of formula (I):

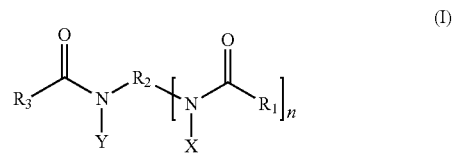

in which:
- $R_1$ and $R_3$ denote, independently of each other, an alkyl radical containing from 1 to 25 carbon atoms;
- $R_2$ denotes a spacer formed from a linear or branched alkylene chain containing from 1 to 12 carbon atoms;
- X and Y denote, independently of each other, a group $—(C_2H_4O)_a—(C_3H_6O)_bZ$ in which
  - Z denotes a hydrogen atom or a radical $—CH_2—COOM$, $—SO_3M$, $—P(O)(OM)_2$, $—C_2H_4—SO_3M$, $—C_3H_6—SO_3M$ or $—CH_2(CHOH)_4CH_2OH$, in which M, M' represent H or an alkali metal, alkaline-earth metal, ammonium or alkanolammonium ion,
  - a ranges from 0 to 15,
  - b ranges from 0 to 10, and
  - the sum of a+b ranges from 1 to 25; and
- n ranges from 1 to 10.

Since the composition of the invention is intended especially for topical application, it comprises a physiologically acceptable medium, i.e. a medium that is compatible with all keratin materials such as the skin, the nails, mucous membranes and keratin fibres (such as the hair and the eyelashes).

The composition obtained according to the invention has the advantage of having a uniform, non-tacky texture that is very soft on application to the skin and after penetration of the product, without a dragging or coarse effect on the skin.

A subject of the invention is also a cosmetic process for treating keratin materials, which consists in applying to the keratin materials a composition as defined above.

Superabsorbent Polymer

The term "superabsorbent polymer" means a polymer that is capable in its dry form of spontaneously absorbing at least 20 times its own weight of aqueous fluid, in particular of water and especially of distilled water. Such superabsorbent polymers are described in the book "Absorbent polymer technology, Studies in polymer science 8" by L. Brannon-Pappas and R. Harland, published by Elsevier, 1990.

These polymers have a large capacity for absorbing and retaining water and aqueous fluids. After absorption of the aqueous liquid, the polymer particles thus engorged with aqueous fluid remain insoluble in the aqueous fluid and thus conserve their individualized particulate state.

The superabsorbent polymer may have a water-absorbing capacity ranging from 20 to 2000 times its own weight (i.e. 20 g to 2000 g of absorbed water per gram of absorbent polymer), preferably from 30 to 1500 times and better still from 50 to 1000 times. These water absorption characteristics are defined under standard temperature (25° C.) and pressure (760 mmHg, i.e. 100 000 Pa) conditions and for distilled water.

The value of the water-absorbing capacity of a polymer may be determined by dispersing 0.5 g of polymer(s) in 150 g of a water solution, waiting for 20 minutes, filtering the unabsorbed solution through a 150 μm filter for 20 minutes and weighing the unabsorbed water.

The superabsorbent polymer used in the composition of the invention is in the form of particles. Preferably, the particles of superabsorbent polymer in dry or unhydrated form have a mean size of less than or equal to 100 μm, preferably less than or equal to 50 μm, for example ranging from 10 to 100 μm, preferably from 15 to 50 μm and better still from 20 to 30 μm.

The mean size of the particles in dry form corresponds to the mass-average diameter ($D_{50}$) measured by laser granulometry or another equivalent method known to those skilled in the art.

These particles, once hydrated, swell forming soft beads with a mean size that may range from 10 μm to 1000 μm.

Preferably, the superabsorbent polymers used in the present invention are in the form of spherical particles.

The superabsorbent polymers that may be used in the composition according to the invention may be chosen especially from:
- crosslinked sodium polyacrylates, for instance those sold under the brand names Octacare X100, X110 and RM100 by the company Avecia, those sold under the names Flocare GB 300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/sodium acrylate copolymer) by the company Grain Processing, or Aqua Keep 10 SH NF sold by the company Sumitomo Seika,
- starches grafted with an acrylic polymer (homopolymer or copolymer) and especially with sodium polyacrylate, such as those sold under the names Sanfresh ST-100C, ST100MC and IM-300MC by the company Sanyo Chemical Industries (INCI name: Sodium polyacrylate starch),
- hydrolysed starches grafted with an acrylic polymer (homopolymer or copolymer) and especially acryloacrylamide/sodium acrylate copolymer, such as those sold under the names Water Lock A-240, A-180, B-204, D-223, A-100, C-200 and D-223 by the company Grain Processing (INCI name: Starch/acrylamide/sodium acrylate copolymer),
- polymers based on starch, gum and cellulose derivative, such as the product containing starch, guar gum and sodium carboxymethylcellulose, sold under the name Lysorb 220 by the company Lysac,
- and mixtures thereof.

The superabsorbent polymers used in the present invention may or may not be crosslinked. They are preferably chosen from crosslinked polymers.

The superabsorbent polymers used in the present invention are preferably chosen from crosslinked, preferably neutralized, acrylic homopolymers or copolymers.

Preferably, the superabsorbent polymer is chosen from crosslinked sodium polyacrylates, preferably in the form of particles with a mean size of less than or equal to 100 microns, more preferably in the form of spherical particles. These polymers preferably have a water-absorbing capacity from 10 to 100 g/g, preferably from 20 to 80 g/g and better still from 50 to 70 g/g.

The superabsorbent polymer may be present in the composition of the invention in an active material content ranging, for example, from 0.05% to 15% by weight, preferably from 0.1% to 10% by weight, preferably ranging from 0.1% to 5% by weight, preferentially ranging from 0.1% to 3% by weight, or even from 0.5% to 2% by weight relative to the total weight of the composition.

Gemini Surfactant

The gemini surfactant of formula (I) is preferably such that each of the groups $R_1$—CO— and $R_3$—CO— comprises from 8 to 20 carbon atoms, and preferably denotes a coconut fatty acid residue (predominantly comprising lauric acid and myristic acid).

In addition, this surfactant is preferably such that, for each of the radicals X and Y, the sum of a and b has a mean value ranging from 10 to 20 and is preferably equal to 15. A preferred group for Z is the group —$SO_3M$ in which M is preferably an alkali metal ion such as a sodium ion.

The spacer $R_2$ is advantageously formed from a linear $C_1$-$C_3$ alkylene chain and preferably an ethylene chain ($CH_2CH_2$).

Finally, n is advantageously equal to 1.

A surfactant of this type is in particular the one identified by the INCI name: Sodium dicocoylethylenediamine PEG-15 sulfate, having the following structure:

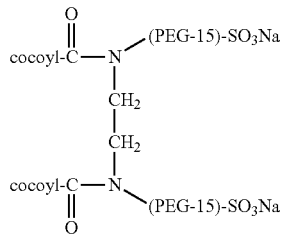

it being understood that PEG represents the group $CH_2CH_2O$ and cocoyl represents the coconut fatty acid residue.

This surfactant has a molecular structure very similar to that of ceramide-3.

Preferably, the gemini surfactant according to the invention is used as a mixture with other surfactants, and especially as a mixture with (a) an ester of a $C_6$-$C_{22}$ fatty acid (preferably $C_{14}$-$C_{20}$ such as a stearate) and of glycerol, (b) a diester of a $C_6$-$C_{22}$ fatty acid (preferably $C_{14}$-$C_{20}$ such as a stearate) and of citric acid and glycerol (especially a diester of a $C_6$-$C_{22}$ fatty acid and of glyceryl monocitrate), and (c) a $C_{10}$-$C_{30}$ fatty alcohol (preferably behenyl alcohol).

Advantageously, the composition according to the invention comprises a mixture of sodium dicocoylethylenediamine PEG-15 sulfate, glyceryl stearate, glyceryl stearate monocitrate and behenyl alcohol.

More preferentially, the gemini surfactant according to the invention represents from 10% to 20% by weight and advantageously 15% by weight; the ester of a $C_6$-$C_{22}$ fatty acid and of glycerol represents from 30% to 40% by weight and advantageously 35% by weight; the diester of a $C_6$-$C_{22}$ fatty acid and of citric acid and glycerol represents from 10% to 20% by weight and advantageously 15% by weight; and the $C_{10}$-$C_{30}$ fatty alcohol represents from 30% to 40% by weight and advantageously 35% by weight, relative to the total weight of the surfactant mixture containing the gemini surfactant.

Advantageously, the composition according to the invention comprises a mixture of 10% to 20% by weight of sodium dicocoylethylenediamine PEG-15 sulfate, from 30% to 40% (in particular 35%) by weight of glyceryl stearate, from 10% to 20% (in particular 15%) by weight of glyceryl stearate monocitrate, from 30% to 40% (in particular 35%) by weight of behenyl alcohol, relative to the total weight of the surfactant mixture containing the gemini surfactant.

As a variant, the gemini surfactant according to the invention may be used as a mixture with an anionic surfactant such as a lauric acid ester or sodium lauroyl lactate. In this case, the gemini surfactant preferably represents from 30% to 50% by weight and the anionic surfactant represents from 50% to 70% by weight, relative to the total weight of the mixture.

It is possible, for example, to use the gemini surfactant as a mixture with other surfactants in the form of the products sold by the company Sasol under the name Ceralution®, and especially the following products:

Ceralution® H: Behenyl Alcohol, Glyceryl Stearate, Glyceryl Stearate Citrate and Sodium Dicocoylethylenediamine PEG-15 Sulfate, Ceralution® F: Sodium Lauroyl Lactylate and Sodium Dicocoylethylenediamine PEG-15 Sulfate.

Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names).

This gemini surfactant represents from 3% to 50% of the weight of these mixtures.

The gemini surfactant of formula (I) may be present in the composition according to the invention in a content ranging from 0.05% to 10% by weight relative to the total weight of the composition, preferably ranging from 0.1% to 5% by weight and better still ranging from 0.2% to 2% by weight.

Aqueous Phase

The aqueous phase of the compositions according to the invention comprises at least water. Depending on the galenical form of the composition, the amount of aqueous phase may range from 0.1% to 99% by weight, preferably from 0.5% to 98% by weight, better still from 30% to 95% by weight and even better still from 40% to 95% by weight relative to the total weight of the composition. This amount depends on the desired galenical form of the composition. The amount of water may represent all or part of the aqueous phase, and is generally at least 30% by weight relative to the total weight of the composition.

The aqueous phase may comprise at least one hydrophilic solvent, for instance substantially linear or branched lower monoalcohols containing from 1 to 8 carbon atoms, for instance ethanol, propanol, butanol, isopropanol or isobutanol; polyols such as propylene glycol, isoprene glycol, butylene glycol, propylene glycol, glycerol, sorbitol or polyethylene glycols and derivatives thereof, and mixtures thereof.

Fatty Phase

The proportion of the fatty phase of the emulsion may range, for example, from 1% to 80% by weight, preferably from 2% to 50% by weight and better still from 5% to 30% by weight relative to the total weight of the composition.

This indicated amount does not include the content of lipophilic surfactants.

The nature of the fatty phase (or oily phase) of the emulsion is not critical. The fatty phase may thus be formed from any fatty substance conventionally used in cosmetics or dermatology, and especially comprises at least one oil (fatty substance that is liquid at 25° C.).

As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil or shea butter oil;

synthetic esters and synthetic ethers, especially of fatty acids, for instance oils of formulae $R^aCOOR^b$ and $R^aOR^b$ in which $R^a$ represents the fatty acid residue containing from 8 to 29 carbon atoms and $R^b$ represents a branched or unbranched hydrocarbon-based chain containing from 3 to 30 carbon atoms, for instance purcellin oil, isononyl isononanoate, isopropyl myristate, 2-ethylhexyl palmitate; 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

substantially linear or branched hydrocarbons of mineral or synthetic origin, such as volatile or non-volatile liquid paraffins, and derivatives thereof, petroleum jelly, polydecenes, isohexadecane, isododecane and hydrogenated polyisobutene such as Parleam® oil;

fatty alcohols containing from 8 to 26 carbon atoms, for instance cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol;

alkoxylated fatty alcohols and especially ethoxylated fatty alcohols, such as oleth-12, ceteareth-12 and ceteareth-20;

partially hydrocarbon-based and/or partially silicone-based fluoro oils, for instance those described in document JP-A-2 295 912. Examples of fluoro oils that may also be mentioned include perfluoromethylcyclopentane and perfluoro-1,3-dimethylcyclohexane, sold under the names Flutec PC1® and Flutec PC3® by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane sold under the name MSX 4518® by the company 3M and nonafluoroethoxyisobutane; perfluoromorpholine derivatives, such as the 4-trifluoromethylperfluoromorpholine sold under the name PF 5052® by the company 3M;

silicone oils, for instance volatile or non-volatile polymethylsiloxanes (PDMSs) containing a substantially linear or cyclic silicone chain, that are liquid or pasty at room temperature, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, that are pendant or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes; mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin, beeswax, carnauba wax or candelilla wax, paraffin waxes, lignite wax or microcrystalline waxes, ceresin or ozokerite, synthetic waxes such as polyethylene waxes and Fischer-Tropsch waxes; liquid petroleum paste.

These fatty substances may be chosen in a varied manner by a person skilled in the art so as to prepare a composition having the desired properties, for example in terms of consistency or texture.

In a known manner, all the compositions of the invention may contain one or more adjuvants that are common in cosmetics and dermatology, hydrophilic or lipophilic gelling agents and/or thickeners; moisturizers; emollients; hydrophilic or lipophilic active agents; free-radical scavengers; sequestrants; antioxidants; preserving agents; acidifying or basifying agents; fragrances; film-forming agents; dyestuffs (pigments such as iron oxides and titanium dioxide, nacres and soluble dyes); fillers; and mixtures thereof.

The amounts of these various adjuvants are those conventionally used in the fields under consideration. In particular, the amounts of active agents vary according to the desired aim and are those conventionally used in the fields under consideration, for example from 0.1% to 20% and preferably from 0.5% to 10% relative to the total weight of the composition.

As hydrophilic gelling agents other than the polymers described above, examples that may be mentioned include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers sold under the name Sepigel 305 (CTFA name: polyacrylamide/C13-14 isoparaffin/Laureth-7) or Simulgel 600 (CTFA name: acrylamide/sodium acryloyldimethyltaurate copolymer/isohexadecane/polysorbate 80) by the company SEPPIC; cellulose derivatives such as hydroxyethylcellulose; polysaccharides and especially gums such as xanthan gum; and mixtures thereof.

Lipophilic gelling agents that may be mentioned include modified clays such as hectorite and its derivatives, for instance the products sold under the name Bentone.

Active Agents

According to the invention, the term "hydrophilic active agent" means a compound having a solubility in water of at least 0.25% at room temperature (25° C.). In addition, according to the invention, the term "oxidation-sensitive hydrophilic active agent" means any active agent of natural or synthetic origin that can undergo degradation via a mechanism of oxidation. This oxidation phenomenon may have several causes, in particular the presence of oxygen, light, metal ions, a high temperature, or certain pH conditions.

Examples of oxidation-sensitive hydrophilic active agents that may be mentioned, in a non-limiting manner, include ascorbic acid and its derivatives such as 5,6-di-O-dimethylsilyl ascorbate (sold by the company Ste Exsymol under the reference PRO-AA), the potassium salt of dl-α-tocopheryl 21-ascorbyl phosphate (sold by the company Senju Pharmaceutical under the reference Sepivital EPC), magnesium ascorbyl phosphate and sodium ascorbyl phosphate (sold by the company Roche under the reference Stay-C 50); phloroglucinol; enzymes; and mixtures thereof. According to one preferred embodiment of the invention, ascorbic acid is used among the oxidation-sensitive hydrophilic active agents. The ascorbic acid may be of any nature. Thus, it may be of natural origin in powder form or in the form of orange juice, preferably concentrated orange juice. It may also be of synthetic origin, preferably in powder form.

As other active agents that may be used in the composition of the invention, examples that may be mentioned include moisturizers such as protein hydrolysates and polyols, for instance glycerol, glycols, for instance polyethylene glycols; natural extracts; anti-inflammatory agents; procyannidol oligomers; vitamins, for instance vitamin A (retinol), vitamin E (tocopherol), vitamin B5 (panthenol), vitamin B3 (niacinamide) and derivatives of these vitamins (especially esters), and mixtures thereof; urea; caffeine; depigmenting agents such as kojic acid, hydroquinone and caffeic acid; salicylic acid and its derivatives; α-hydroxy acids such as lactic acid and glycolic acid and derivatives thereof; retinoids such as carotenoids and vitamin A derivatives; hydrocortisone; melatonin; algal extracts, fungal extracts, plant extracts, yeast extracts and bacterial extracts; steroids; antibacterial active agents, for instance 2,4,4'-trichloro-2'-hydroxydiphenyl ether (or triclosan), 3,4,4'-trichlorocarbanilide (or triclocarban) and the acids indicated above and especially salicylic acid and its derivatives; matting agents, for instance fibres; tensioning agents; and mixtures thereof.

Screening Agents:

The composition may comprise at least one UV-screening agent, which may be chosen from organic and inorganic screening agents, in particular from organic screening agents. The organic screening agents may be chosen from lipophilic and hydrophilic organic screening agents, or mixtures thereof.

The term "lipophilic screening agent" means any screening agent that is capable of being completely dissolved in molecular form in a liquid fatty phase or of being dissolved in colloidal form (for example in micellar form) in a liquid fatty phase.

The term "hydrophilic UV-screening agent" means any agent for screening out UV radiation that can be completely dissolved in molecular form in the aqueous phase of the emulsion or that can be dissolved in colloidal form (for example in micellar form) in the aqueous phase of the emulsion.

Preferably, the composition comprises at least one lipophilic organic screening agent.

The lipophilic organic screening agents may be chosen from para-aminobenzoic acid derivatives, salicylic derivatives, cinnamic derivatives, benzophenones and aminobenzophenones, anthranilic derivatives, dibenzoylmethane derivatives, β,β-diphenylacrylate derivatives, benzylidenecamphor derivatives, phenylbenzimidazole derivatives, benzotriazole derivatives, triazine derivatives, bis-resorcinyl triazines, imidazoline derivatives, benzalmalonate derivatives, 4,4-diarylbutadiene derivatives, benzoxazole derivatives, merocyanins, diphenylbutadiene malonate or malononitrile derivatives and chalcones, and mixtures thereof.

Among the lipophilic UVA screening agents capable of absorbing UV from 320 to 400 nm, mention may be made of:

Dibenzoylmethane Derivatives:
4-isopropyldibenzoylmethane, sold under the name Eusolex 8020 by the company Merck, and corresponding to the following formula:

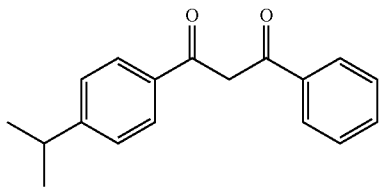 [SMILES: CC(C)c1ccc(C(=O)CC(=O)c2ccccc2)cc1]

1-(4-methoxy-1-benzofuran-5-yl)-3-phenylpropane-1,3-dione, sold by the company Quest under the name Pongamol, of formula:

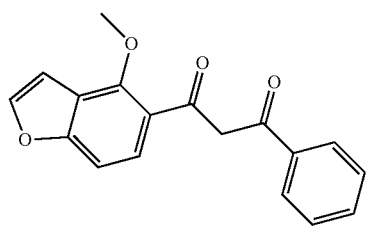 [SMILES: COc1c(C(=O)CC(=O)c2ccccc2)ccc2occc12]

1-(4-tert-butylphenyl)-3-(2-hydroxyphenyl)propane-1,3-dione of formula:

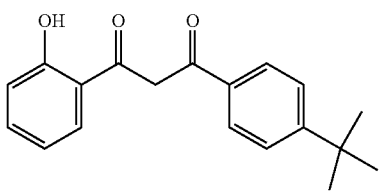 [SMILES: CC(C)(C)c1ccc(C(=O)CC(=O)c2ccccc2O)cc1]

butylmethoxydibenzoylmethane sold especially under the trade name Parsol 1789 by Hoffmann LaRoche, Aminobenzophenones:
n-hexyl 2-(4-diethylamino-2-hydroxybenzoyl)benzoate sold under the trade name Uvinul A+

Anthranilic Derivatives:
menthyl anthranilate sold under the trade name Neo Heliopan MA by Haarmann & Reimer, 4,4-Diarylbutadiene Derivatives:
1,1-dicarboxy(2,2'-dimethylpropyl)-4,4-diphenylbutadiene The preferred products are:
Among the lipophilic UVB screening agents capable of absorbing UV from 280 to 320 nm, mention may be made of:

para-Aminobenzoates:
ethyl PABA
ethyl dihydroxypropyl PABA
ethylhexyl dimethyl PABA (Escalol 507 from ISP)

Salicylic Derivatives:
Homosalate sold under the name Eusolex HMS by Rona/EM Industries,
ethylhexyl salicylate sold under the name Neo Heliopan OS by Haarmann & Reimer,
dipropylene glycol salicylate sold under the name Dipsal by Scher,
TEA Salicylate sold under the name Neo Heliopan TS by Haarmann & Reimer, Cinnamates:
ethylhexyl methoxycinnamate sold especially under the trade name Parsol MCX by Hoffmann LaRoche,
isopropyl methoxycinnamate,
isoamyl methoxycinnamate sold under the trade name Neo Heliopan E 1000 by Haarmann & Reimer,
diisopropyl methylcinnamate,
Cinoxate,
glyceryl ethylhexanoate dimethoxycinnamate β,β'-Diphenylacrylate Derivatives:
Octocrylene, sold especially under the trade name Uvinul N539 by BASF,
Etocrylene, sold especially under the trade name Uvinul N35 by BASF, Benzylidenecamphor Derivatives:
3-benzylidenecamphor manufactured under the name Mexoryl SD by Chimex,
methylbenzylidenecamphor sold under the name Eusolex 6300 by Merck,
polyacrylamidomethylbenzylidenecamphor manufactured under the name Mexoryl SW by Chimex, Triazine Derivatives:
ethylhexyl triazone sold especially under the trade name Uvinul T150 by BASF,
diethylhexyl butamido triazone sold under the trade name Uvasorb HEB by Sigma 3V,
2,4,6-tris(dineopentyl 4'-aminobenzalmalonate)-s-triazine,
2,4,6-tris(diisobutyl 4'-aminobenzalmalonate)-s-triazine,
2,4-bis(dineopentyl 4'-aminobenzalmalonate)-6-(n-butyl 4'-aminobenzoate)-s-triazine,
2,4-bis(n-butyl 4'-aminobenzoate)-6-(aminopropyltrisiloxane)-s-triazine, Imidazoline Derivatives:
ethylhexyl dimethoxybenzylidene dioxoimidazoline propionate, Benzalmalonate Derivatives:
polyorganosiloxanes containing a benzalmalonate function, such as Polysilicone-15 sold under the trade name Parsol SLX by Hoffmann LaRoche dineopentyl 4'-methoxybenzalmalonate, Merocyanin Derivatives:
octyl-5-N,N-diethylamino-2-phenysulfonyl-2,4-pentadienoate Among the lipophilic broad-spectrum screening agents capable of absorbing UVA and UVB, mention may be made of:

Benzophenone Derivatives:
Benzophenone-1 sold under the trade name Uvinul 400 by BASF,
Benzophenone-2 sold under the trade name Uvinul D50 by BASF,
Benzophenone-3 or Oxybenzone, sold under the trade name Uvinul M40 by BASF,
Benzophenone-6 sold under the trade name Helisorb 11 by Norquay,
Benzophenone-8 sold under the trade name Spectra-Sorb UV-24 by American Cyanamid,
Benzophenone-10,
Benzophenone-11,
Benzophenone-12, Benzotriazole Derivatives:

Drometrizole Trisiloxane sold under the name Silatrizole by Rhodia Chimie,

Bumetrizole sold under the name Tinoguard AS by Ciba-Geigy,

Bis-resorcinyl Triazines:

bis-ethylhexyloxyphenol methoxyphenyl triazine sold under the trade name Tinosorb S by Ciba Geigy, Benzoxazole Derivatives:

2,4-bis-[5-1(dimethylpropyl)benzoxazol-2-yl(4-phenyl)imino]-6-(2-ethylhexyl)imino-1,3,5-triazine sold under the name Uvasorb K2A by Sigma 3V.

The derivatives of the diphenylbutadiene malonate or malononitrile family are the derivatives of general formula (IV):

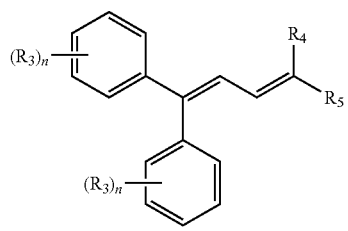

(IV)

in which $R_3$ represents a $C_1$-$C_2$ alkyl group, a $C_1$-$C_2$ alkoxy group and n is equal to 0, 1 or 2;

$R_4$ and $R_5$, which may be identical or different, represent —$COOR_6$, —(C=O)$NHR_6$, —(C=O)$R_6$, —CN in which $R_6$ represents a linear or branched alkyl group containing from 1 to 12 carbon atoms, and possibly containing silane, siloxane or polysiloxane groups.

Among the diphenylbutadiene malonate or malononitrile derivatives, mention may be made especially, in a non-limiting manner, of:

dimethyl 2-(3,3-diphenylprop-2-enylidene)malonate diisobutyl 2-(3,3-diphenylprop-2-enylidene)malonate bis(1,3-dimethylbutyl) 2-(3,3-diphenylprop-2-enylidene)malonate dineopentyl 2-(3,3-diphenylprop-2-enylidene)malonate methyl(2Z)-2-cyano-5,5-diphenylpenta-2,4-dienoate ethyl(trimethylsilyl)methyl(2Z)-2-(3,3-diphenylprop-2-enylidene)malonate (2E)-2-cyano-5,5-diphenyl-N-(3-{1,3,3,3-tetramethyl-1-[(trimethylsilyl)oxy]disiloxanyl}propyl)penta-2,4-dienamide ethyl 2-methyl-3-{1,3,3,3-tetramethyl-1-[(trimethylsilyl)oxy]disiloxanyl}propyl(2E)-2-(3,3-diphenylprop-2-enylidene)malonate ethyl(2Z)-5,5-diphenyl-2-{[(3-{1,3,3,3-tetramethyl-1-[(trimethylsilyl)oxy]-disiloxanyl}propyl)amino]carbonyl}penta-2,4-dienoate Among the diphenylbutadiene derivatives mentioned above, use will be made in particular of dineopentyl 2-(3,3-diphenylprop-2-enylidene)malonate corresponding to the following formula:

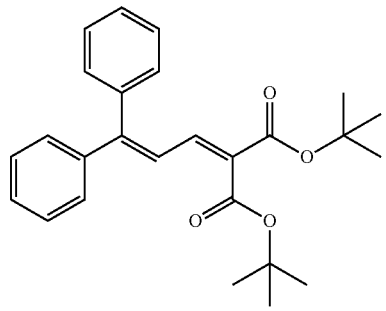 [SMILES: CC(C)(C)OC(=O)C(=CC=C(c1ccccc1)c1ccccc1)C(=O)OC(C)(C)C]

It is known practice to use these diphenylbutadiene derivatives in antisun compositions. Patent EP 0 916 335 describes carbon-based derivatives and methods for obtaining them, and patents EP 1 535 947 and EP 1 535 925 describe the siloxane and silane derivatives, respectively.

The derivatives of the chalcone family are derivatives of general formula (V) below:

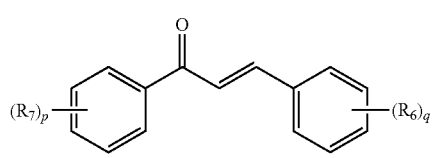

(V)

in which the radicals $R_6$ and $R_7$ denote, independently of each other, a hydrogen atom, a hydroxyl radical, a linear or branched $C_1$-$C_{12}$ alkyl or alkenyl group, a linear or branched $C_1$-$C_{12}$ alkoxy group or a linear or branched $C_2$-$C_{20}$ acyloxy group;

p and q

Among the chalcone derivatives, mention may be made especially, in a non-limiting manner, of:

2'-hydroxychalcone
4'-hydroxychalcone
4'-methoxychalcone
2'-hydroxy-4-methoxychalcone
2'-hydroxy-4-hexyloxychalcone
2'-hydroxy-4-methylchalcone
2'-hydroxy-3-hexyloxychalcone
2'-hydroxy-4'-hexyloxy-4-methylchalcone
2'-hydroxy-4'-hexanoyloxy-4-methoxychalcone
2',4',4-trihydroxy-3,3'-diallylchalcone (known under the name Kazonol)
2',4',4-trihydroxy-5'-(methyl-3-but-2-ene)chalcone (known under the name Broussochalcone B)
2',3',4',6',4-pentahydroxychalcone (known under the name Carthamin)

Among the chalcone derivatives mentioned above, use will be made in particular of 4'-hydroxychalcone corresponding to formula (Va) below:

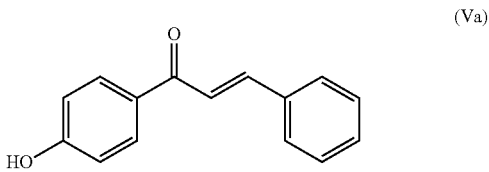 [SMILES: O=C(/C=C/c1ccccc1)c1ccc(O)cc1]

(Va)

or 2',3',4',6',4-pentahydroxychalcone (known under the name Carthamin) corresponding to formula (Vb) below:

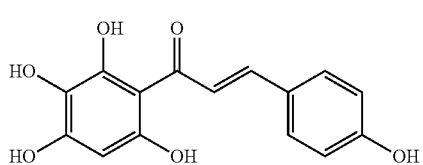

It is known practice to use these chalcone derivatives in antisun compositions, especially in patents FR 2 555 167, FR 2 602 228 and FR 2 608 150.

The lipophilic organic UV-screening agent may be preferably chosen from:
- salicylic derivatives, in particular homosalate and ethylhexyl salicylate,
- cinnamic derivatives, such as ethylhexyl methoxycinnamate,
- β,β'-diphenylacrylate derivatives such as octocrylene,
- dibenzoylmethane derivatives such as methoxydibenzoylmethane,
- triazine derivatives such as ethylhexyl triazone and diethylhexyl butamidotriazone,
- benzotriazole derivatives such as drometrizole trisiloxane,
- and mixtures thereof.

Among the hydrophilic or water-soluble UV-screening agents that may be used according to the invention, mention may be made of the following screening agents denoted below under their INCI name:
- water-soluble UVA screening agents capable of absorbing UV from 320 to 400 nm, such as:
- terephthalylidenedicamphorsulfonic acid manufactured under the name Mexoryl SX by Chimex,
- bis-benzoazolyl derivatives as described in patents EP 669 323 and U.S. Pat. No. 2,463,264 and more particularly the compound disodium phenyldibenzimidazole tetrasulfonate sold under the trade name Neo Heliopan AP by Haarmann & Reimer,
- water-soluble UVB screening agents capable of absorbing UV from 280 to 320 nm, such as: p-aminobenzoic (PABA) derivatives, for instance PABA, glyceryl PABA, and PEG-25 PABA sold under the name Uvinul P25 by BASF,
- phenylbenzimidazolesulfonic acid sold especially under the trade name Eusolex 232 by Merck,
- ferulic acid
- salicylic acid
- DEA methoxycinnamate
- benzylidenecamphorsulfonic acid manufactured under the name Mexoryl SL by Chimex,
- camphorbenzalkonium methosulfate manufactured under the name Mexoryl SO by Chimex, and
- water-insoluble UVA and UVB screening agents, such as Benzophenone-4 sold under the trade name Uvinul MS40 by BASF,
- Benzophenone-5, and
- Benzophenone-9.

The insoluble organic UV-screening agents may be chosen especially from insoluble organic UV-screening agents of oxalanilide, vinyl amide, cinnamide, benzazole, benzofuran, arylvinylidene ketone, acrylonitrile amide, acrylonitrile sulfonamide, acrylonitrile carbamate or phenylene-bis-benzoxazinone type.

The organic screening agents are generally present in the compositions according to the invention in proportions ranging from 0.05% to 30% by weight relative to the total weight of the composition, preferably ranging from 0.1% to 20% by weight and better still from 0.5% to 15% by weight relative to the total weight of the composition.

Inorganic UV-screening agents that may be mentioned include metal oxide particles with a mean elementary particle size of less than or equal to 500 nm, more preferentially between 5 nm and 500 nm, even more preferentially between 10 nm and 100 nm and preferentially between 15 and 50 nm. They may be chosen especially from titanium, zinc, iron, zirconium and cerium oxides, or mixtures thereof. Depending on their more or less pronounced lipophilic, or on the other hand hydrophilic, nature, the mineral screening agents may be present either in the fatty phase of the emulsion or in the aqueous phase, or even in both phases at once.

As fillers that may be used in the composition of the invention, examples that may be mentioned include pigments such as titanium oxide, zinc oxide or iron oxide and organic pigments; kaolin; silica; talc; boron nitride; organic spherical powders, fibres; and mixtures thereof. Examples of organic spherical powders that may be mentioned include polyamide powders and especially Nylon® powders such as Nylon-1 or Polyamide 12, sold under the name Orgasol by the company Atochem; polyethylene powders; Teflon®; microspheres based on acrylic copolymers, such as those made of ethylene glycol dimethacrylate/lauryl methacrylate copolymer, sold by the company Dow Corning under the name Polytrap; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; polymethyl methacrylate microspheres, sold under the name Microsphere M-100 by the company Matsumoto or under the name Covabead LH85 by the company Wackherr; ethylene acrylate copolymer powders, such as those sold under the name Flobeads by the company Sumitomo Seika Chemicals; powders of natural organic materials such as starch powders, especially of corn starch, wheat starch or rice starch, which may or may not be crosslinked, such as the starch powders crosslinked with octenyl succinate anhydride, sold under the name Dry-Flo by the company National Starch. Examples of fibres that may be mentioned include polyamide fibres, especially such as Nylon 6 (or Polyamide 6) (INCI name: Nylon 6) fibres, Nylon 6,6 (or Polyamide 66) (INCI name: Nylon 66) fibres, or such as poly-p-phenyleneterephthamide fibres; and mixtures thereof. These fillers may be present in amounts ranging from 0 to 20% by weight and preferably from 0.5% to 10% by weight relative to the total weight of the composition.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

The compositions according to the invention may be in the form of emulsions of liquid or semi-liquid consistency, for example of the milk type, obtained by dispersing a fatty phase in an aqueous phase (O/W) or conversely (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

According to one preferred embodiment of the invention, the composition is in the form of an O/W emulsion.

In addition, the compositions used according to the invention may be more or less fluid and may have the appearance of a gel, a white or coloured cream, a pomade, a milk, a lotion, a serum, a paste or a mousse.

The composition preferably has a skin-friendly pH that generally ranges from 3 to 8 and preferably from 4.5 to 7.

The examples that follow will allow the invention to be understood more clearly, without, however, being limiting in nature. The amounts indicated are weight percentages, unless otherwise mentioned.

EXAMPLES 1 TO 3

Moisturizing O/W Emulsions

A composition according to the invention (Example 1) comprising a gemini surfactant and a superabsorbent polymer, and two comparative compositions (Examples 2 and 3) comprising a gemini surfactant and acrylic polymers that are not superabsorbent, are prepared:

| Phase | | Example 1 (invention) | Example 2 (comparative) | Example 3 (comparative) |
|---|---|---|---|---|
| A | Water | qs 100 | qs 100 | qs 100 |
|   | Preserving agents | qs | qs | qs |
| B | Isononyl isononanoate | 4 | 4 | 4 |
|   | Hydrogenated isoparaffin | 5 | 5 | 5 |
|   | Polymethylene wax | 2 | 2 | 2 |
|   | Cetyl alcohol | 0.5 | 0.5 | 0.5 |
|   | Gemini surfactant at 15% AM* (Ceralution ® H from the company Sasol) | 2 | 2 | 2 |
| C | Glycerol | 3 | 3 | 3 |
|   | Crosslinked polyacrylate microspheres at 89% active material as a mixture with silica in water (Aqua Keep 10 SH NF from Sumitomo Seika) | 0.8 | — | — |
|   | Crosslinked sodium polyacrylate at 90% dry matter in water (Cosmedia SP from Cognis) | — | — | 0.8 |
|   | Acrylic homopolymer at 98% dry matter in water (Carbopol 980 from Lubrizol) | | 0.8 | |
|   | Sodium hydroxide | | 0.3 | |

*active material

Procedure

Heat phase A to 85° C. and then cool to 75° C.
Heat phase B to 75° C.
In a mixer, add phase B to phase A at 75° C.
With Rayneri blending, add phase C to the mixture (A+B) and then allow to cool to room temperature with Rayneri blending.

These compositions were evaluated by 10 individuals, who applied each product to the back of their hands.

The composition of Example 1 according to the invention was judged as being more glidant on application, softer and less tacky after penetration of the product into the skin, compared with the compositions of Examples 2 and 3.

EXAMPLES 4 TO 6

SPF 25 Antisun O/W Emulsions

A composition according to the invention (Example 4) comprising a lipophilic screening agent and a superabsorbent polymer, and two comparative compositions (Examples 5 and 6) comprising a gemini surfactant and acrylic polymers that are not superabsorbent, are prepared:

| Phase | | Example 4 (invention) | Example 5 (comparative) | Example 6 (comparative) |
|---|---|---|---|---|
| A | Water | qs 100 | qs 100 | qs 100 |
|   | Preserving agents | qs | qs | qs |
| B | Isononyl isononanoate | 2 | 2 | 2 |
|   | Poly($C_{10-30}$ alkyl acrylate) (Intelimer IPA 13-1 from Air Products) | 2 | 2 | 2 |
|   | Cetyl alcohol | 0.5 | 0.5 | 0.5 |
|   | Gemini surfactant at 15% AM (Ceralution ® H from the company Sasol) | 3 | 3 | 3 |
|   | Octocrylene | 7 | 7 | 7 |
|   | Ethylhexyl salicylate (Neo Heliopan OS from Haarmann & Reimer) | 5 | 5 | 5 |
|   | Butylmethoxydibenzoyl-methane (Parsol 1789 from Hoffmann LaRoche) | 3 | 3 | 3 |
| C | Glycerol | 2 | 2 | 2 |
|   | Propylene glycol | 2 | 2 | 2 |
|   | Disodium EDTA | 0.1 | 0.1 | 0.1 |
|   | Crosslinked polyacrylate microspheres at 89% active material as a mixture with silica in water (Aqua Keep 10 SH NF from Sumitomo Seika) | 0.8 | — | — |
|   | Crosslinked sodium polyacrylate at 90% dry matter in water (Cosmedia SP from Cognis) | — | — | 0.8 |
|   | Ammonium polyacryldimethyl-tauramide (Hostacerin AMPS) | | 0.8 | |

Procedure

Heat phase A to 85° C. and then cool to 75° C.
Heat phase B to 75° C.
In a mixer, add phase B to phase A at 75° C.
With Rayneri blending, disperse phase C in the mixture (A+B) and then cool to room temperature with Rayneri blending.

The composition of Example 4 according to the invention was judged as being more glidant on application, softer and less tacky after penetration of the product into the skin, compared with the compositions of Examples 5 and 6.

The invention claimed is:

1. Cosmetic compositions in emulsion form comprising at least one aqueous phase and at least one fatty phase, at least one superabsorbent polymer and at least one surfactant of formula (I):

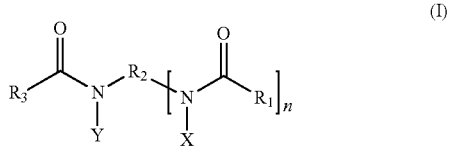

(I)

in which:
R1 and R3 denote, independently of each other, an alkyl radical containing from 1 to 25 carbon atoms;
R2 denotes a spacer formed from a linear or branched alkylene chain containing from 1 to 12 carbon atoms;
X and Y denote, independently of each other, a group $-(C_2H_4O)_a-(C_3H_6O)_bZ$ in which
Z denotes a hydrogen atom or a radical $-CH_2-COOM$, $-SO_3M$, $P(O)(OM)_2$, $-C_2H_4-SO_3M$, $-C_3H_6-SO_3M$ or $CH_2(CHOH)_4CH_2OH$, in which M, M' represent H or an alkali metal, alkaline-earth metal, ammonium or alkanolammonium ion,
a ranges from 0 to 15,
b ranges from 0 to 10, and
the sum of a+b ranges from 1 to 25; and
n ranges from 1 to 10; wherein the surfactant of formula (I) is at least one gemini surfactant.

2. Composition according to claim 1, wherein the superabsorbent polymer is in the form of particles having in dry form a mean size of less than or equal to 100 μm.

3. Composition according to claim 1, wherein the superabsorbent polymer is in the form of particles having in dry form a mean size ranging from 10 to 100 μm.

4. Composition according to claim 1, wherein the superabsorbent polymer has a water-absorbing capacity of from 50 to 1000 times its own weight.

5. Composition according to claim 1, wherein the superabsorbent polymer is chosen from crosslinked sodium polyacrylates, starches grafted with an acrylic polymer, hydrolysed starches grafted with an acrylic polymer, and polymers based on starch, gum and cellulose derivative, and mixtures thereof.

6. Composition according to claim 1, wherein the superabsorbent polymer is crosslinked.

7. Composition according to claim 1, wherein the superabsorbent polymer is chosen from crosslinked acrylic homopolymers or copolymers.

8. Composition according to claim 1, wherein the superabsorbent polymer is chosen from crosslinked sodium polyacrylates.

9. Composition according to claim 1, wherein the superabsorbent polymer is in the form of spherical particles.

10. Composition according to claim 1, wherein the superabsorbent polymer is present in an active material content ranging from 0.05% to 15% by weight relative to the total weight of the composition.

11. Composition according to claim 1, wherein, for the gemini surfactant of formula (I), each of the groups $R_1-CO-$ and $R_3-CO-$ denotes a coconut fatty acid residue.

12. Composition according to claim 1, wherein, for the gemini surfactant of formula (I), for each of the radicals X and Y, the sum of a and b has a mean value ranging from 10 to 20.

13. Composition according to claim 1, wherein, for the gemini surfactant of formula (I), Y is a group $-SO_3M$ in which M is an alkali metal ion such as a sodium ion.

14. Composition according to claim 1, wherein, for the gemini surfactant of formula (I), n is equal to 1.

15. Composition according to claim 1, wherein the surfactant of formula (I) has the following structure:

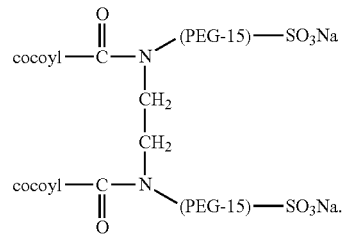

16. Composition according to claim 1, wherein the gemini surfactant is mixed with (a) an ester of a $C_6$-$C_{22}$ fatty acid and of glycerol, (b) a diester of a $C_6$-$C_{22}$ fatty acid and of citric acid and glycerol, and (c) a $C_{10}$-$C_{30}$ fatty alcohol.

17. Composition according to claim 1, wherein the gemini surfactant is present in a content ranging from 0.05% to 10% by weight relative to the total weight of the composition.

18. Cosmetic process for treating a keratin material, wherein a cosmetic composition as defined according to claim 1 is applied to the keratin material.

19. Composition according to claim 2, wherein the superabsorbent polymer is in the form of particles having in dry form a mean size ranging from 10 to 100 μm.

20. Composition according to claim 2, wherein the superabsorbent polymer has a water-absorbing capacity of from 50 to 1000 times its own weight.

21. Composition according to claim 1, wherein the emulsion is an oil-in-water emulsion, wherein the superabsorbent polymer is present in an active material content ranging from 0.1% to 10% by weight relative to the total weight of the composition, and wherein the gemini surfactant is present in a content ranging from 0.1% to 5% by weight relative to the total weight of the composition.

22. Composition according to claim 21, wherein the superabsorbent polymer is present in an active material content ranging from 0.1% to 5% by weight relative to the total weight of the composition, and wherein the gemini surfactant is present in a content ranging from 0.2% to 2% by weight relative to the total weight of the composition.

23. Composition according to claim 22, wherein the superabsorbent polymer is present in an active material content ranging from 0.1% to 3% by weight relative to the total weight of the composition.

24. Composition according to claim 22, wherein the superabsorbent polymer is present in an active material content ranging from 0.5% to 2% by weight relative to the total weight of the composition.

* * * * *